US009031296B2

(12) United States Patent
Kaempfer et al.

(10) Patent No.: US 9,031,296 B2
(45) Date of Patent: May 12, 2015

(54) METHOD AND SYSTEM FOR ERROR RESILIENT COMPRESSION AND DECOMPRESSION OF COMPUTED TOMOGRAPHY DATA

(75) Inventors: Gideon Kaempfer, Raanana (IL); Anatoli Rapoport, Rehovot (IL); Yariv Michaeli, Kfar Vradim (IL); Tomer Margolin, Tel Aviv (IL)

(73) Assignee: Xring Technologies GmbH (DE)

( * ) Notice: Subject to any disclaimer, the term of this patent is extended or adjusted under 35 U.S.C. 154(b) by 460 days.

(21) Appl. No.: 13/424,578

(22) Filed: Mar. 20, 2012

(65) Prior Publication Data

US 2012/0237101 A1    Sep. 20, 2012

Related U.S. Application Data

(63) Continuation of application No. PCT/IB2010/002361, filed on Sep. 21, 2010.

(51) Int. Cl.

| | |
|---|---|
| *A61B 6/03* | (2006.01) |
| *G06T 9/00* | (2006.01) |
| *H04N 19/50* | (2014.01) |
| *H04N 19/91* | (2014.01) |
| *A61B 6/00* | (2006.01) |

(Continued)

(52) U.S. Cl.
CPC . *A61B 6/032* (2013.01); *A61B 6/56* (2013.01); *A61B 6/482* (2013.01); *G06F 19/321* (2013.01); *G06T 9/004* (2013.01); *G06T 9/005* (2013.01); *H03M 7/40* (2013.01); *H04N 19/50* (2014.11); *H04N 19/12* (2014.11); *H04N 19/91* (2014.11); *H04N 19/436* (2014.11)

(58) Field of Classification Search
None
See application file for complete search history.

(56) References Cited

U.S. PATENT DOCUMENTS

| | | | |
|---|---|---|---|
| 5,764,374 A | 6/1998 | Seroussi et al. | |
| 5,825,830 A | 10/1998 | Kopf | |

(Continued)

FOREIGN PATENT DOCUMENTS

DE    10 2007 014830    8/2008

OTHER PUBLICATIONS

Weinberger et al. "The LOCO-I Lossless Image Compression Algorithm: Principles and Standardization into JPEG-LS." IEEE Transactions on Image Processing, vol. 9, No. 8, Aug. 2000, pp. 1309-1324.*

(Continued)

*Primary Examiner* — Jon Chang
(74) *Attorney, Agent, or Firm* — Yakov Sidorin; Quarles & Brady LLP

(57) ABSTRACT

A method and system for transferring data from a rotating data source to a stationary target over a slip ring. The system includes a compressor on a rotor, a decompressor on a stationary platform, and respectively corresponding memory buffers. The data is optionally compressed in the event that the slip ring capacity is below the required rate. The compressor a predictor unit, an entropy encoder unit and an error protector unit. The predictor unit may use stored data as reference from a set of frames and locations within them. Encoding of locations may be carried out with a Golomb-Rice encoded integer, and entropy encoding of differences may involve Golomb-Rice encoding with parameter K varying for each group of data units. The error protector protects parameters inserted into data stream with an error protection code while most of the data can remain without protection.

39 Claims, 6 Drawing Sheets

(51) Int. Cl.
*G06F 19/00* (2011.01)
*H03M 7/40* (2006.01)
*H04N 19/12* (2014.01)
*H04N 19/436* (2014.01)

(56) References Cited

U.S. PATENT DOCUMENTS

| | | | | |
|---|---|---|---|---|
| 6,470,065 | B1* | 10/2002 | Lauther | 378/4 |
| 6,654,419 | B1 | 11/2003 | Sriram | |
| 2006/0262859 | A1* | 11/2006 | Ishikawa | 375/240.23 |
| 2007/0248271 | A1* | 10/2007 | Sakai et al. | 382/236 |
| 2009/0046913 | A1* | 2/2009 | Chandra | 382/131 |
| 2009/0169119 | A1* | 7/2009 | Wegener | 382/232 |
| 2010/0128998 | A1* | 5/2010 | Wegener et al. | 382/248 |
| 2011/0026591 | A1* | 2/2011 | Bauza et al. | 375/240.12 |

OTHER PUBLICATIONS

Golomb, S.W., "Run-Length Encodings", IEEE Transactions on Information Theory, Jul. 1966, pp. 399-401

Weinberger, et al., "LOCO-I: A Low Complexity, Context-Based, Lossless Image Compression Algorithm", Hewlett-Packard Laboratories, Palo Alto, CA, 11 pages.
Rice, Robert, "Some Practical Universal Noiseless Coding Techniques", National Aeronautics and Space Administration, Jet Propulsion Laboratory, Pasadena CA, Mar. 15, 1979, 130 pages.
Rice, Robert, "Some Practical Universal Noiseless Coding Techniques, Part III, Module OS114,K+", National Aeronautics and Space Administration, Jet Propuision Laboratory, Pasadena CA, Nov. 15, 1991, 134 pages.
The International Search Report as mailed on Feb. 15, 2011 for International Application No. PCT/IB2010/002361.
Shaou-Gang Miaou, et al., "A Lossless Compression Method for Medical Image Sequences Using JPEG-LS and Interframe Coding," IEEE Transactions on Information Techonology in Biomedicine, IEEE Service Center, Los Alamitos, CA, U.S., vol. 13, No. 5, Sep. 1, 2009, pp. 818-821, XP011293613.
Philips, W., et al., "State-of-the-art Techniques for Lossless Compression of 3D Medical Image Sets," Computerized Medical Imaging and Graphics, Pergamon Press, New York, NY, U.S., vol. 25, Jan. 1, 2001, pp. 173-185, XP007916939.

* cited by examiner

METHOD AND SYSTEM FOR ERROR RESILIENT COMPRESSION AND DECOMPRESSION OF COMPUTED TOMOGRAPHY DATA

PRIORITY CLAIM

This application is a continuation of pending International Application No. PCT/IB2010/002361 filed on Sep. 21, 2010, which designates the United States and claims priority from U.S. provisional Patent Application No. 61/244,276 filed on Sep. 21, 2009.

BACKGROUND OF THE INVENTION

1. Field of the Invention

The present invention relates generally to the art of medical diagnostic imaging and baggage imaging and in particular to a method and apparatus for a computer tomography of the type wherein the measurement data are compressed and possibly decompressed en route to the computer that reconstructs images of the scanned object.

2. Description of Relevant Art

In Computer Tomography (CT), raw data is acquired during a scan of an object irradiated by X-rays from an X-ray source from different directions (projections) and the X-rays attenuated by the object are incident on a number of sensors (channels) that are arranged in multiple rows of a radiation detector. The number of rows is typically referred to as the number of slices.

The X-ray source and the detector are mounted on a rotor or gantry. Accordingly, for every rotor position, multiple vectors of data corresponding to the number of slices, also known as "fan" or "reading" are obtained. During a scan, the rotor is rotated in angular steps, each step giving a new reading. The set of readings for one full turn of the rotor is referred to as "rotation". During or after a full rotation, the object to be examined (patient) is moved in a direction orthogonal to the rotors plane and data accumulated over many rotations is combined into one file that is accompanied by a file meta-data and additional meta-data for each vector.

In CT scans having 672 sensors with 128 slices there are 672*128 channels and may be 2320 readings per rotation. Accordingly, 199557120 measurements per rotation are obtained with each measured value stored as an unsigned word of 16 bit (2 bytes). Thus, there are roughly 400 MByte of data per rotation. The number of rotations depends on the size of the patient to be scanned, (for example approximately 10 to 20 rotations are required for scanning a human head). As such, a substantially high rate of data is generated that in turn is transmitted to a central processing unit for a reconstruction of the scanned object's images.

Therefore, compression methods capable of efficiently compressing this data en route to the computer can improve on the overall operation of CT imaging devices by reducing the storage space and bandwidth required for transmission of the data to the central processing unit.

CT imaging as a medical tool is well known for its benefits in medical analysis but at the same time, due to the use of X-rays, it is also known as harmful to the human (or other live object) being scanned. For this reason, in order to maximize the medical benefit from the minimal harm done, regulation requires that meaningful data obtained from a scan should not be lost. Sources of data loss may include lossless compression techniques as well as data corruption typically inevitable due to physical limitations of transmission means. Such transmission means typically ensure bit error rates below 1 part in 1,000,000,000,000 (10 to the power of 12) but not zero. For the size of data passed in a CT scan and calculated above (4 GByte), this implies that one in every few tens of scans may suffer one or more bit corruptions.

Due to the requirement not to lose meaningful data, compression algorithms for CT image data are preferably, albeit not exclusively, lossless compression algorithms. In addition, error detection and correction schemes should be used in order to protect against the unfortunate event of data corruption.

Several compression algorithms for CT imaging data have been proposed in the art. Most such algorithms, if not all of them, consist of three main steps: A first step where a prediction is made regarding the anticipated data, a second step where the data to be compressed is compared to the prediction and a third step where the difference between the data to be compressed and the predicted data is encoded as efficiently as possible (typically called the entropy encoding step).

Typical algorithms predict data based on previously stored data, and frequently encode image pixels based on multiple image pixels from the past. For example, the LOCO-I algorithm as disclosed in the U.S. Pat. No. 5,764,374 encodes pixels based on a group of pixels adjacent to the predicted pixel. As a result, the corruption of a single bit in compressed data, may affect more than a single pixel within the represented data because during decompression, a corrupted pixel may affect pixels surrounding it. Therefore, in typical compression algorithms, compressed data is more sensitive to the inevitable data corruption than non-compressed data. On the other hand, error detection and correction schemes, such as Reed Solomon or Hamming codes require the addition of significant data to the protected data, reducing the effectiveness of compression.

Thus, a need arises to find a technique for compression resulting in compressed data that is as sensitive to data corruption as non-compressed data while preserving high lossless compression ratios.

A slip ring (in electrical engineering terms) is an apparatus for making an electrical connection through a rotating assembly. Slip rings are also referred to as rotary electrical interfaces, rotating electrical connectors, collectors, swivels or electrical rotary joints. A slip ring consists of a conductive circle or band mounted on a shaft and insulated from it. Electrical connections from the rotating part of the system, such as the rotor of a generator, are made to the ring. Fixed contacts or brushes run in contact with the ring, transferring electrical power or signals to the exterior, static part of the system. In essence, a slip ring is the equivalent of a power and communications cable with the ability to traverse a rotating joint without getting tangled up. Furthermore contactless data and power transmission systems are used, herein also referred as slip rings. An example is disclosed in US 20030185427 A1.

Slip rings are frequently used in CT scanners in order to connect between the rotor of the scanner which generates CT raw data and the stationary central processing unit which is used to reconstruct and display 3D images from this data.

Current slip rings are limited in their data throughput to about 10 Gigabits per second (10 Gbps which is 10E9 bits per second). For some high resolution CT scans this bandwidth isn't sufficient in order to transfer raw data and display CT images in real time on the stationary display. Hence, compression is useful in virtually expanding the communications capacity of a slip ring.

Compression algorithms are by definition dependent on the data they need to compress. It is well known in the art that for any compression algorithm there exists data which cannot be compressed at all and in particular cannot be compressed above a given threshold ratio. Hence, a system that is designed to be dependent on a minimal compression ratio that can always be achieved may fail when data to be compressed fails to compress at the required ratio. This is true in particular to CT scanners that employ compression.

Without prior knowledge of scanned objects and the data generated by scanning them with a CT scanner, a CT scanner design would need to assume compression may not be effective at all, and hence taking worst case scenarios into consideration would eliminate the main benefit of compression— the ability to use relatively low throughput communications links for high bandwidth communications.

SUMMARY OF THE INVENTION

The embodiments are based on the object of designing a method and a system architecture to cope with low compression periods without losing data while maintaining the benefit of compression during all other periods. Other aspects of the invention are a compressor and a decompressor supporting the system architecture.

Disclosed herein are exemplary methods and systems for transferring data from a rotating data source such as an X-ray scanner to a stationary target such as a central processing unit over a slip ring. Specifically a method for compressing data, a method for decompressing data, a data compressor, a decompressor, a system for compressing and decompressing data, a slip ring having a system for compressing and decompressing data and a CT scanner having a system for compressing and decompressing data are disclosed.

Solutions of the problem are described in the independent claims. The dependent claims relate to further improvements of the invention.

A compressing slip ring system is disclosed comprising a compressor located on a rotating platform connected to a data generator from which it receives data, a slip ring split between such rotating platform and a stationary platform connecting between both platforms and a decompressor located on such stationary platform connected to a target via a communications network.

A compressor for a compressing slip ring system may comprise of any of the features disclosed in here.

A decompressor for a compressing slip ring system may comprise of any of the features disclosed in here.

A CT scanner comprising a compressing slip ring system may comprise of any of the features disclosed in here. Here the data generator is a digital sampler of analog signals received by a signal receiver from an X-ray detector.

A method for compressing sampled analog data comprises receiving and processing data in the form of pixels associated to a given image frame and location within the frame. The data are predicted based on a reference to one of a set of F previously stored frames and one of multiple potential coordinates within such frames expressed by means of a vector V that is encoded as a positive integer. Error protection may be applied to the encoded data.

Furthermore, the compressor or the compressing slip ring may comprise memory buffers attached to at least one of the compressor or the decompressor.

A compressor may comprise at least one of a predictor, an entropy encoder and an error protector.

The predictor may handle incoming data in groups of data pixels and may predict the incoming data pixels based on one of a set of F previously stored frames and one of multiple potential coordinates within such frames. The one of such set of F previously stored frames may be just the one before last frame.

Preferably groups of pixels of size G belonging to a single image row or a single image column are processed together. In a further embodiment pixels of the same pixel cell are processed together. Preferably a single set of F, V, K, P and possibly other parameters are attached to them.

The coordinates within such frames may be expressed by means of a vector V that is encoded as a positive integer. In turn, the positive integer may be encoded using Golomb-Rice encoding with a parameter $K_v$.

The entropy encoder may either encode groups of differences received from the predictor using Golomb-Rice encoding with a parameter $K_{min}$ which may be different for every group of differences or may forward data as is in non-compressed format in the event that Golomb-Rice encoding results in more data than non-compressed data.

In addition, the entropy encoder may embed the parameter $K_{min}$ within the data it applies to using a minimal encoding that also indicates the case where no compression is used.

The entropy encoder may forward data as is in non-compressed format once every S frames. Data forwarded as is may be a subset of pixel groups within every frame.

The entropy encoder may select a subset of pixel groups by just choosing a pixel group every S groups where S is a prime number that does not divide the number of groups in a single frame. This selection does not take the association to frame into account but just sees the groups as an infinite sequence of groups. The result is that each group related to specific coordinates in a frame is selected exactly once per S frames.

Instead of sending the selected groups as non-compressed data, the predictor may further compress the group, but instead of using a best prediction derived from reference (history) data, the predictor uses a fixed value as reference. This results in a worst case where data is not compressed, but frequently allows compression of these groups based on internal similarity within the group.

The error protector may protect a subset of data being sent with the encoded data by an error correction code. Such subset of data protected by such error correction code may be limited to at most one or more of $K_{min}$ and other parameters encoded within the data stream but need not be applied to all the compressed data. In particular, error protection may be performed by means of a Hamming code.

In addition, a method is disclosed for compressing sampled analog data by receiving and processing data in the form of pixels associated to a given image frame and location within the frame; predicting the data based on a reference to one of a set of F previously stored frames and one of multiple potential coordinates within such frames; selecting the best prediction and encoding its location in history $F_{min}$ and $V_{min}$; encoding the difference between the prediction and the incoming data using a set of parameters $K_{min}$ and P added into the output data stream; and finally protecting a subset of the output data from errors by means of an error correction code.

Processing and selecting of pixels may be performed in groups of size G and the one of a set of previously stored frames may be the frame before last.

The coordinates within the selected reference frame may be expressed as a vector V that may be encoded as a positive integer, in turn encoded using Golomb-Rice encoding with a parameter $K_v$.

The encoding of difference may be performed using a Golomb-Rice encoding with a parameter $K_{min}$ which may be different for every such group of differences or by retaining the input data in its non-compressed format in the event that Golomb-Rice encoding results in more data than the non-compressed data.

The parameter $K_{min}$ may be encoded with the data it applies to using a minimal encoding that also indicates the case where no compression is used.

The encoding may retain data as is in non-compressed format once every S frames. Such retention of data may be performed for a subset of pixel groups within every frame.

The encoding may select a subset of pixel groups by just choosing a pixel group every S groups where S is a prime number that does not divide the number of groups in a single frame. This selection does not take the association to frame into account but just sees the groups as an infinite sequence of groups. The result is that each group related to specific coordinates in a frame is selected exactly once per S frames.

Instead of sending the selected groups as non-compressed data, the encoding may further compress the group, but instead of using a best prediction derived from reference (history) data, the encoding uses a fixed value as reference. This results in a worst case where data is not compressed, but frequently allows compression of these groups based on internal similarity within the group.

Finally, the subset of protected output data may be limited to at most one or more of $K_{min}$, $F_{min}$ and $V_{min}$. Such subset of protected output data may be protected by means of a Hamming error protection code.

BRIEF DESCRIPTION OF THE DRAWINGS

In the following, the invention will be described by way of example, without limitation of the general inventive concept, on examples of embodiment and with reference to the drawings.

Figure 1:
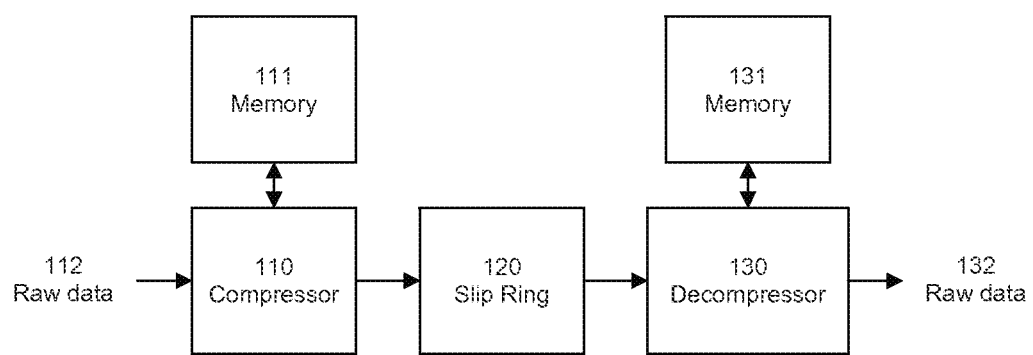
FIG. 1 is a block diagram with relevant elements of a compressing slip ring system.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the figures in which like numerals represent like elements throughout the several views, exemplary embodiments of the present invention are described. For convenience, only some elements of the same group may be labeled with numerals. The purpose of the drawings is to describe exemplary embodiments.

FIG. 1 is an exemplary embodiment of a system titled a compressing slip ring. It consists of a compressor 110 with memory 111 included or attached to it, a slip ring 120 and a decompressor 130 with memory 131 included or attached to it.

The compressor 110 may be located on a rotating platform, referred to as the rotor, from which raw data 112 is obtained such as data from X-ray sensors on a computer tomography scanner, also referred to as data generator. The compressor receives such raw data and may store it in its attached memory 111. In one embodiment, the compressor 110 may be implemented on a single Field Programmable Logic Array (FPGA) device. In other embodiments it may be implemented on an Application Specific Integrated Circuit (ASIC) on multiple FPGA's or ASIC's or in software on a CPU or System on Chip (SoC). In one embodiment, either memory 111, 131 may be implemented on the same device as the compressor or decompressor (i.e. in on-die memory). In other embodiments, the memory may be implemented on one or more memory devices such as DRAM devices assembled next to the compressor 110 on the same Printed Circuit Board (PCB) or on a PCB connected to the PCB on which the compressor or decompressor resides.

The memory 111 may be used by the compressor 110 in order to store historical raw data as reference for compression as well as a temporary buffer used for data before or after compression in cases where the compressor cannot immediately transmit data over the slip ring, for instance due to throughput limits of the slip ring.

The memory 131 may be used by the decompressor 130 in order to store data in events where such target, or network leading to such target, are not capable of receiving the data at the rate produced by the decompressor.

The size of the memory 111 may be determined based on the maximum size of backlogged data resulting from throughput bottlenecks, worst case compression ratios and the absolute size of raw data anticipated. For instance, if a maximum of 4 GByte of data is anticipated per CT scan, data is generated over a period of 2 seconds (at a rate of 16 Gbps), the slip ring capacity is 8 Gbps and worst case compression ratio on average is 1.6:1, this would imply that effective throughput over the slip ring would be 12.8 Gbps in the worst case (in terms of raw data) and effective accumulation rate of compressed raw data would be of 2 Gbps (16 Gbps of raw data becomes 10 Gbps post compression of which 8 Gbps of compressed data may be transmitted in real time). Over a scan of two seconds, this would imply 4 Gbit of data accumulation and a memory buffer requirement of 512 Mbyte. However, if it is also known, for example as the result of more careful analysis, that worst case compression ratios only appears over less than 10% of the scan duration and that average compression ratios exceed 2:1, significantly smaller memory buffers may be required, even in the order of just a few megabytes, which could easily fit in existing FPGA devices.

Returning to FIG. 1, the compressor 110 may transmit compressed data over the slip ring 120 towards the decompressor 130 which may store data in attached memory buffers 131. The decompressor 130 delivers at its output uncompressed raw data 132. Furthermore compressed data may be stored on the stationary unit or any storage element for further use.

The decompressor 130 may be located on a stationary unit, referred to as the stator, from which raw data may be sent to a central processing unit or server for data analysis and display or to a storage element such as a disk array, Network Attached Storage (NAS) or a Storage Area Network (SAN). The decompressor receives compressed raw data and may store it or its decompressed version of data in its attached memory 131. In one embodiment, the decompressor 130 may be implemented on a single Field Programmable Logic Array (FPGA) device. In other embodiments it may be implemented on an Application Specific Integrated Circuit (ASIC) on multiple FPGA's or ASIC's or in software on a CPU or System on Chip (SoC). In one embodiment, the memory 131 may be implemented on the same device as the decompressor (i.e. in on-die memory). In other embodiments, the memory may be implemented on one or more memory devices such as DRAM devices assembled next to the decompressor 130 on the same Printed Circuit Board (PCB) or on a PCB connected to the PCB on which the decompressor resides.

In yet another embodiment, it is envisioned that the decompressor 130 would communicate via a communications protocol over the slip ring 120 with the compressor 110 and control the rate of data flow such that (compressed) data would arrive at the decompressor just in time for it to decompress it and forward it towards its eventual target (as mentioned above). In such a case, the communications protocol would act as a flow control or back pressure mechanism which would limit data transmission over the slip ring 120 in cases where the communications means from the decompressor to its target are more limited than the rate of raw data generated by the decompressor post decompression. This would be specifically useful if the decompressor may not have any memory attached to it, or very little memory attached to it.

In another embodiment, the decompressor 130 may also use the abovementioned communications protocol in order to request that the compressor 110 retransmit compressed data which has been corrupted while traveling over the communications link between them. The detection of such corruption can leverage error detection and correction data attached to the compressed data (see below).

In another embodiment, the decompressor 130 may not communicate with the compressor 110 over the slip ring 120. In such case, the memory 131 attached to the decompressor may serve to store compressed data or decompressed data prior to its transmission to its final destination. The size of such memory may be determined based on the anticipated rate of incoming (compressed) data, the rate of transmission possible to the target, the rate at which the target may successfully process or store incoming data, the best and worst case compression ratios and the rate at which raw data is generated. For instance, if the maximum allowed rate of data over the slip ring 120 is limited to 8 Gbps (of compressed data), the rate at which transmission towards the target is limited to 10 Gbps (of decompressed data), the rate of processing at the target is limited to 8 Gbps (of decompressed data) and the best case compression ratio is 3:1 and worst case compression ratio is 1.6:1 (as in the example above), for a scan of up to 4 Gbyte over a period of two seconds (implying a raw data generation rate of 16 Gbps) one could deduce the required memory as follows: The maximum rate for the decompressor to transmit to the target is 8 Gbps (the minimum of the 10 Gbps communications rate and 8 Gbps processing rate) and since the raw data rate is limited by the generator to 16 Gbps, average accumulation is limited to 8 Gbps (16 Gbps generation rate minus 8 Gbps transmission rate) which may be stored in compressed format with a ratio of at least 1.6:1. Hence, compressed data may be accumulated at 8/1.6=5 Gbps over a period of two seconds resulting in 10 Gbit or 1.25 GByte.

In another embodiment, the compressor 110 may be configured with known decompressor communications throughput towards the target as well as with its attached memory 131 capacity. In such case, the compressor may include logic that limits data rates towards the decompressor such as to limit memory requirements at the decompressor without need for the decompressor to communicate its actual memory requirements towards the compressor.

In yet another embodiment, if the decompressor is configured not to decompress data, the central processing unit or storage target may store data in a compressed format. As a result, transmission and processing overheads may be eliminated resulting in lower memory requirements at the decompressor, which under some circumstances may even become negligible even if no flow control communications protocol is used between the decompressor and the compressor.

It is noted that the compressing slip ring depicted in FIG. 1 may expose external interfaces which are identical to slip ring interfaces as known in the art. These interfaces may include fiber optic or electrical interfaces. As such, the compressing slip ring may be offered as a drop in replacement for conventional slip ring sub-systems with the benefit of higher effective throughput and effectively without the risk of data loss in the event of exposure to non-compressible or badly compressible data.

Figure 2:
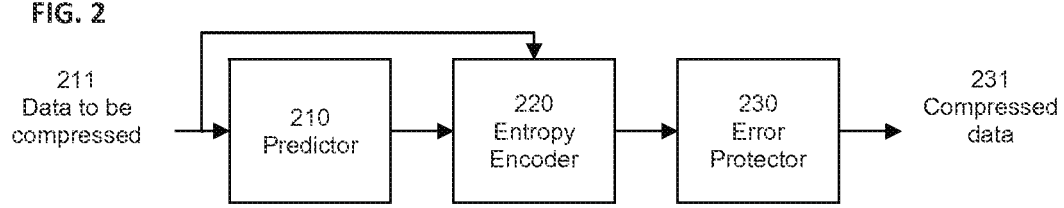
FIG. 2 is a block diagram with relevant elements of a compressor system.

Reference is now made to FIG. 2 which depicts an exemplary embodiment of a compressor. Such a compressor may be employed for image compression as well as other types of data. In the context of this application data to be compressed will be referred to as pixels representing single elements within an image. However, it should be appreciated that other types of data may also be compressed in similar fashion even if such data doesn't represent an image. For instance, such data may represent any type of data including digitally sampled data from a variety of sources such as light, electromagnetic radiation or audio. Preferably the data to be compressed is scaled before compressing. Such a scaling may comprise adding or subtracting of an offset value and/or multiplying with a scaling value and/or applying of a transfer function. In the specific case of a CT scanner by scaling the signals of different physical detector modules having different scintillators or different signal processing components may be equalized. Equalization may be based on reference measurements with the same detector(s) or with reference detector(s). The compressor may compress data in the format of fixed point e.g. 16 bit or floating point (e.g. 12 bit mantissa, 4 bit exponent). In case of fixed point data a conversion to floating point may precede the compression. In case of floating point data the mantissa and exponent may be compressed by two different compressors using different algorithms or settings. Alternatively the compression is only applied to mantissa or exponent depending on compression efficiency. Furthermore different compression algorithms may be used for offset, full-scale and imaging (modulated) data sets.

Control data, which may be transmitted separated from image data may be left uncompressed. Control data is data for controlling the hardware like the X-ray tube, processor hardware or the software like the compressor.

The compressor in FIG. 2 comprises a Predictor 210 which receives the data to be compressed 211 in the format of pixels as well as synchronization information regarding the location of such pixels within a possible image frame of given dimensions and form. The main goal of the Predictor is to predict the data to be compressed based on an internal model typically based on the history of incoming data. The output of the predictor is the difference between the incoming data and the predicted model which is sent to the Entropy Encoder 220 for encoding. The Entropy Encoder 220 encodes the difference data coming from the Predictor 210 into a compressed form resulting in compressed data. This data is then sent to an Error Protector 230 which annotates the incoming data with selective error protection code in order to protect the compressed data from a variety of errors. Finally the Error Protector 230 delivers the compressed and optionally error protected data 231 as output of the compressor.

Figure 3:
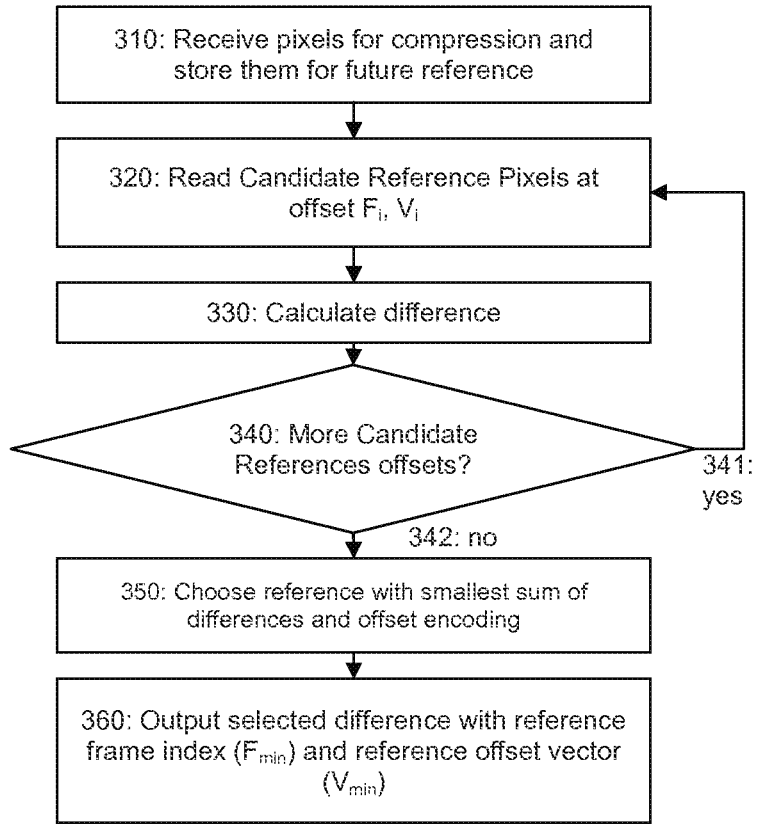
FIG. 3 illustrates a flowchart with relevant steps of a procedure for predicting a group of pixels to be compressed with the use of pixels previously stored in memory.

Reference is now made to FIG. 3 which depicts an exemplary embodiment of a Predictor flow chart.

First the Predictor receives the incoming data in the form of pixels and stores them for future reference 310. A typical pixel may be represented by 16 bits (2 bytes). Pixels may be stored with reference to their image frame (a two dimensional array) and multiple frames may be stored together. Frames are the equivalent of images while multiple frames are the equivalent of a video sequence. Frames may be stored in typical First In First Out (FIFO) order implying that the number of frames to be stored F governs the size of the memory and the length of the "video" stored. A typical number F would be 3 such that new pixels are written over pixels three frames in the past.

Pixels are processed in groups of given size. The size of the group may vary and is typically a divisor of the number of pixels per image row size. However, any number of pixels per group may be used. For example, pixels may be processed in groups of 16 pixels at a time. The size of the group will later govern the relative data overhead associated with meta-data to be attached to the group of pixels after they are compressed. On the other hand, the smaller the group, the higher the probability of correlation between characteristics of such pixels. Hence, a group size reflects a tradeoff between the compression quality achievable per pixel and the overhead associated with achieving the compression. Furthermore, it is appreciated that the groups of pixels of size G processed together may belong to a single image row, a single image column or any other form such as a rectangle that may be tiled upon an image. Preferred group sizes are 16×1, 21×1, 25×1, 32×1 or 42×1.

In a further embodiment the group size is adapted to the pixel cell size of the physical assembly of the detector array. Such a pixel cell size may be given by the size of array of detectors using identical scintillator materials like materials cut from the same crystal or monolithical crystals. It may also be given by separators like grooves and plates to separate neighbored channels for increasing the crosstalk there between. The number of pixels in a cell is preferably a power of two $2^N$ as this is representing the most common detector array structures. Another limit of pixel cell size may be at the border of an array of detectors consisting of one monolithic photo diode array. Further limits may be given by detectors which signals are processed by the same analog preprocessing IC (multiplexer, integrator, sample and hold), the same A/D converter or detectors which are powered by the same power supply.

Next, a group of pixels stored in the past is read from memory to be used as potential reference for comparison 320. Reference pixel groups may be identical in size to the group to be processed. They may be taken from at least one of several previously stored frames, and in particular, not necessarily from the previously stored frame. For instance, if F is 3, reference pixel group may be taken from one of two reference frames—the previous ($F_1$) and before previous frame ($F_2$). In general, for a given F, any pixel group from frames $F_i$ may be taken where $1<=i<=F-1$. In addition, the pixels from the currently processed frame ($F_0$) may also be used as reference, as long as no circular dependency is created.

In a preferred embodiment the pixels of the frame before the last frame are used to reference to a related image which has been generated by a dual tube, dual energy or dual detector CT scanner. As an alternative there may be used a plurality of, preferably two parallel data streams being handled by separated compressors. As a further embodiment a plurality of compression kernels (incorporated in identical or separate parallelized FPGAs) are used parallel to increase compression throughput. The kernels may be adapted to the physical structure of the detector array/CT scanner like division by slices of a multislice detector, or by detectors arrays or by energies if an energy is switched e.g. by a tube with rotating x-ray filter wheel or switched anode voltage or stacked detectors to discriminate the energy.

Within the reference frame, reference pixels may be taken from (x, y) coordinates which are identical to the coordinates of the pixels within the frame being processed or coordinates at a given offset $(x-\Delta x, y+\Delta y)$ from those of the pixels within the frame being processed where $\Delta x$ and $\Delta y$ may be a small positive or negative integers in a predefined range. $\Delta x$ and $\Delta y$ may in turn be expressed in terms of a single integer mapped to the given offsets. Such mapping is depicted for example in FIG. 4 where for example $(\Delta x, \Delta y)=(0,0)$ is encoded as 0, $(\Delta x, \Delta y)=(1,1)$ is encoded as 5, $(\Delta x, \Delta y)=(-1,1)$ is encoded as 8, $(\Delta x, \Delta y)=(-1,-1)$ is encoded as 6, $(\Delta x, \Delta y)=(1,-1)$ is encoded as 7 and $(\Delta x, \Delta y)=(-1,2)$ is encoded as 20. $(\Delta x, \Delta y)=(0,0)$, encoded as 0 represents the input coordinates of the incoming pixel within the frame. Different charts may be used for different applications. V may be encoded using Golomb-Rice encoding with K=Kv. Kv is typically 2 (3-4 bit encoding for most common values). In one embodiment, a mapping representing "good" (see below) reference offsets by smaller integers is preferred. In another embodiment, the only reference offset used is $(\Delta x, \Delta y)=(0,0)$—only the identical coordinates of the pixels being encoded within a previous frame. The mapped integer is hereafter referred to as the vector V from the original coordinates.

In other embodiments, the reference pixels used may be based on combinations of pixels from one or more frames including the current processed frame and frames from the past. For example, V may encode a reference such as the algebraic formula (A+B−C), where A is the pixel at coordinates $(\Delta x, \Delta y)=(-1,0)$ in the current frame being compressed, B is the pixel at coordinates $(\Delta x, \Delta y)=(0,0)$ in the previous frame and C is the pixel at coordinates $(\Delta x, \Delta y)=(-1,0)$ in the previous frame. In another example, V may encode min(A,B) if C>max(A,B), max(A,B) if C<min(A,B) and A+B−C otherwise. Such reference is known in the art as the gradient predictor reference.

In another embodiment the Golomb-Rice encoding may be applied recursively to further decrease code length.

Returning to FIG. 3, for any given vector $V_i$ from a set of allowed vectors, the difference between the pixels to be encoded and their reference pixels selected is calculated 330. In one embodiment, the set of allowed vectors may be for instance the vectors represented by the integers 0-20 in FIG. 4. In another embodiment, only the vector 0 may be used. For the purpose of difference calculation, each pixel is treated as an integer number. For instance, for 16-bit pixels there may be 65536 different possible pixel values ranging from 0 to 65535. The difference between one group of pixels and a reference group of pixels may be expressed as a sum of absolute values of differences between pairs of pixels corresponding to the vector V selected. For example, for a set of four pixels 3, 4, 12, 100 and a reference set of pixels 10, 10, 12, 99 the difference is |3−10|+|4−10|+|12−12|+|100−99|=7+6+0+1=14. Other difference formulas such as mean square, sum of signed differences or size of entropy encodings of differences (see Entropy Encoder below) may also be used.

After calculating a difference 330 it is checked 340 whether there are more candidate references. If there are remaining candidate references 341 the procedure is continued by step 320. If there are no remaining candidate references 342, when all differences at all possible vectors $V_i$ with regard to all possible reference frames $F_i$ have been calculated 340 the pair $(F_i, V_j)$ is chosen for which the difference calculated in 330 is the smallest 350. The selected vector $V_{min}$ and reference frame $F_{min}$ are then encoded and forwarded towards the Entropy Encoder (FIG. 1, 220) together with the calculated differences of the group of pixels for the chosen $(F_{min}, V_{min})$. In one embodiment, $V_{min}$ may be encoded using a Golomb-Rice encoding as known in the art (see below for a more detailed description) with an encoding parameter which may be $K_v=2$. In another embodiment, $F_{min}$ and $V_{min}$ may be fixed to $F_{min}=2$ and $V_{min}=0$. In yet another embodiment, $F_{min}$ may be encoded as one bit representing either $F_{min}=1$ as 0 and $F_{min}=2$ as 1.

Figure 5:
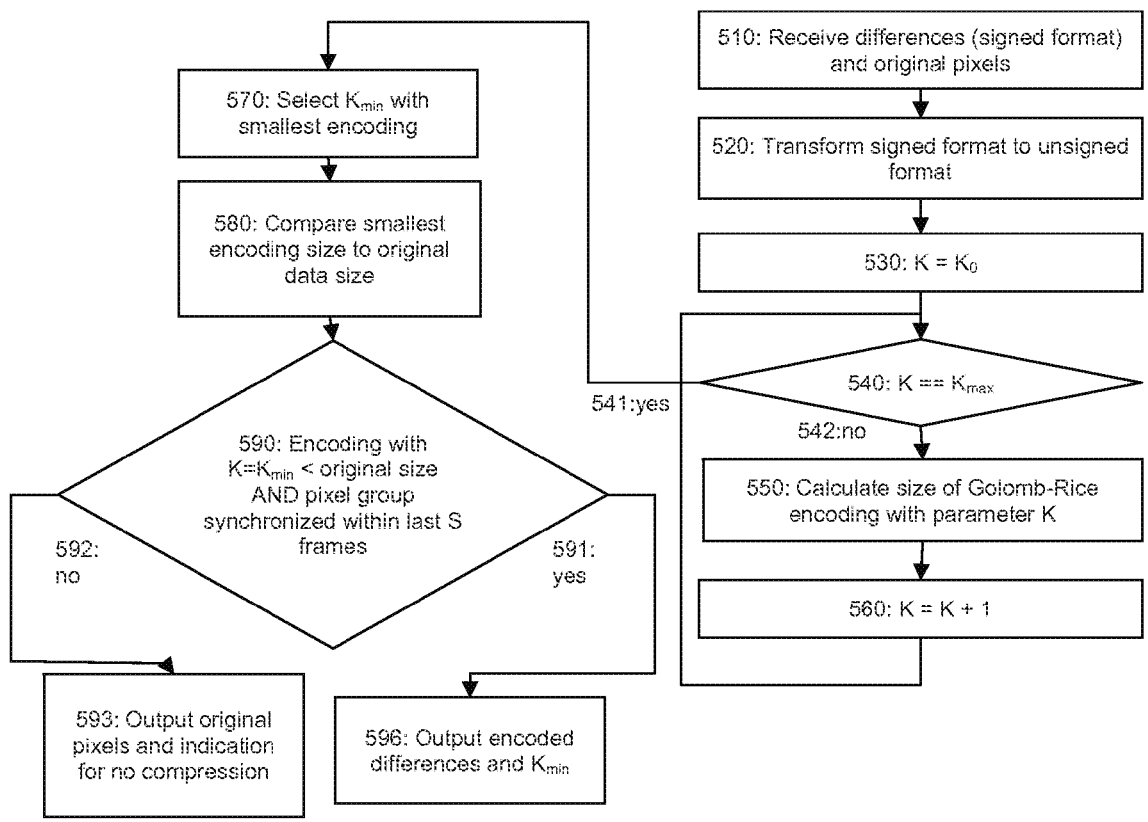
FIG. 5 illustrates a flowchart with relevant steps of a procedure for entropy encoding a group of differences generated by a prediction algorithm.

Reference is now made to FIG. 5 which depicts an exemplary embodiment of an Entropy Encoder flow chart.

The Entropy Encoder (220 in FIG. 2) receives the selected calculated differences from the Predictor (210 in FIG. 2) in a signed format 510 in groups of differences related to groups of pixels as described above. It may also receive original pixels. For pixels represented as N bits (N may be 16 for example), differences may be numbers from $(1-2^N)$ up to $(2^N-1)$ (for N=16 this means from −65535 up to 65535). Thus, differences may be represented as a sign (that may be encoded as a single bit) and N bits representing the absolute value of the difference.

Next, the Entropy Encoder transforms the signed format of the differences into an unsigned format 520. A well known transformation from the art may be used for this such as representing all non-negative differences D by a positive integer 2*D and all negative differences D by a positive integer −2*D−1. For example, a positive difference D=4 may be represented as 2*4=8 and a negative integer D=−2 may be represented as −2*(−2)−1=3. The result is that all negative differences are represented by odd numbers and all non-negative differences are represented by even numbers (zero remains zero). It is noted that following this transformation into non-negative representations, the differences are numbers between 0 and 2(N+1)−2 where N is the number of bits per pixel. Hence they may still be represented by N+1 bits. The value 2(N+1)−1 cannot be a result of the transformation and hence it may be used to indicate an alignment of data into groups or for other purposes. It is noted that other transformations exist but they are quite similar to the above transformation. Any such transformation that transforms small absolute values into small positive integers and large absolute values into large positive integers may be used.

Next, the Entropy Encoder initiates a parameter K into an initial value $K_0$ 530. $K_0$ is typically a small integer such as 3. K is known in the art as the parameter of Golomb-Rice encoding. In this encoding, a positive integer is represented by its K least significant bits followed by the unary representation of its remaining most significant bits followed by a zero bit indicating the end of the unary representation. For example, the number 127 ($1111111_b$ in binary notation) is represented by 1111,1111111,0 for K=4, by 111111,1,0 for K=6 and by 1111111,0 for K=7. This encoding is well known in the art and frequently used in compression algorithms.

Next, the Entropy Encoder calculates the size in bits of the Golomb-Rice encoding with parameter K of the group of differences 550. The K for which a minimal encoding size is achieved is stored as $K_{min}$. The size of the encoding can simply be calculated by adding up the integers represented by the N+1−K most significant bits of the differences (which are represented as integers of N+1 bits) and adding to that G*(K+1) for a group size of G differences (G may be 16 for example). For example, given a group of G=4 differences (5,12,29,31), their representations for K=3 has a size of 0+1+3+3+4*(3+1)=23, their representations for K=4 has a size of 22 and for K=5 has a size of 24. Hence $K_{min}$ in this case is 4.

Next, in one exemplary embodiment, K is incremented by 1 560 and the process of encoding size is repeated for the new K. In another embodiment, the candidate K may be incremented by higher values or by changing values.

If K reaches a predefined maximum value $K_{max}$ in 540 a branch is made to step 570 instead of continuing this step 550. Accordingly no more K's are considered. For example, $K_{max}$ may be set at 10. This implies that values of K are tested between $K_0$ (3 for example) and $K_{max}-1$ (9 for example). In total, the number of K values tested may be any number, and in particular a power of 2 minus 1. For $K_0=3$ and $K_{max}=10$, 7 different values are tested. These values may be represented by a 3 bit integer leaving one 3-bit value unassigned to be used to indicate no compression should be performed (see below).

Next, for the lowest size encoding attained for $K_{min}$, the encoding size is compared with the size of the original incoming data (G*N) for a group of size G and number of bits per pixel of N 580, 590. If the encoded size for $K_{min}$ is larger than or equal to (G*N) 592, no encoding is performed, a fact that may be indicated by the unassigned encoding mentioned above for representing $K_{min}$. In this case the original pixels, and not the differences, may be represented within the outgoing data (no compression will be performed) 593. Otherwise, if the encoded size for $K_{min}$ is smaller than (G*N) 596, the Entropy Encoder may output the encoded $K_{min}$ and the Golomb-Rice encoded differences 596 towards the Error Protector (FIG. 2, 230).

In another embodiment, in addition to the encoding size motivation, the Entropy Encoder may elect to forward the original incoming data at step 590 even if the encoding size for $K_{min}$ is smaller than the size of the original incoming data (G*N). This may be performed every S times a given group of pixels at a given location within a frame needs to be encoded. S may be a predefined parameter of the Entropy Encoder which is intended to ensure that the decompressor can synchronize with the correct data even in the event of data corruption. For instance, if S is set to 100, every 100 frames a pixel group at a given location within a frame may be sent in its non-compressed original format such that no dependency exists on previously transmitted pixels. As a result, even if such pixels may have been corrupted, it is ensured that pixel corruption never affects pixels for more than 100 consecutive frames. The event of sending a non-compressed pixel group is considered a synchronization event between the compressor and the decompressor (or between the Entropy Encoder and the Entropy Decoder).

In one embodiment, a synchronization event may be implemented every S frames for all pixels within the frame. This is the simplest method for implementing synchronization however it also incurs a burst of non-compressed data (an entire non compressed frame is sent). Preferably the synchronization is implemented for each group x within the first frame, assume it has been synchronized ((x mod S)+1) frames ago where S is preferably a prime number. Hence, in another embodiment, synchronization events for different pixel groups within a frame are spread out such that for a frame holding M pixel groups only M/S groups are synchronized for every frame but over a period of S frames all groups are synchronized. In yet another embodiment, the synchronization event of a pixel group within a given frame may be skipped if it was sent in a non-compressed format more recently than S frames ago (e.g. if encoding did not result in a smaller representation than the original input for a recent frame—natural synchronization). This may slightly improve the overall compression ratio without sacrificing error resistance of the encoding.

In one embodiment, if the encoded size after Golomb-Rice encoding for $K_{min}$ is exactly $K_{min}+1$ bits per encoding for all differences encoded within the group (i.e. the most significant bits above the $K_{min}$ least significant bits for all the differences are zero), a special indication may be used to indicate that the encodings are all equal in size and no delimiting bit will be provided with the encodings. This indication may appear in the form of an additional bit marked as P. If P=1, this may indicate normal Golomb-Rice encoding and when P=0 this may indicate that the encodings used for the differences in the group are merely of fixed size representing the $K_{min}$ least significant bits of the differences. The benefit of the P bit may depend on the type of data being compressed. If analysis shows that differences are normally encoded with at least one non zero most significant bit above $K_{min}$ the P bit may be omitted from the data stream. However, if this is not frequently the case, it may be beneficial to include the P bit since it allows reducing the encoding size by G bits for a group of differences of size G.

In one embodiment, the output of the Entropy Encoder may be considered the output of the compressor (FIG. 1, 110). Accordingly the data is transferred to the slip ring without further error protection. In another embodiment, the output of the Entropy Encoder may be delivered to the Error Protector (FIG. 2, 230) for protection against possible bit errors.

Figure 6:
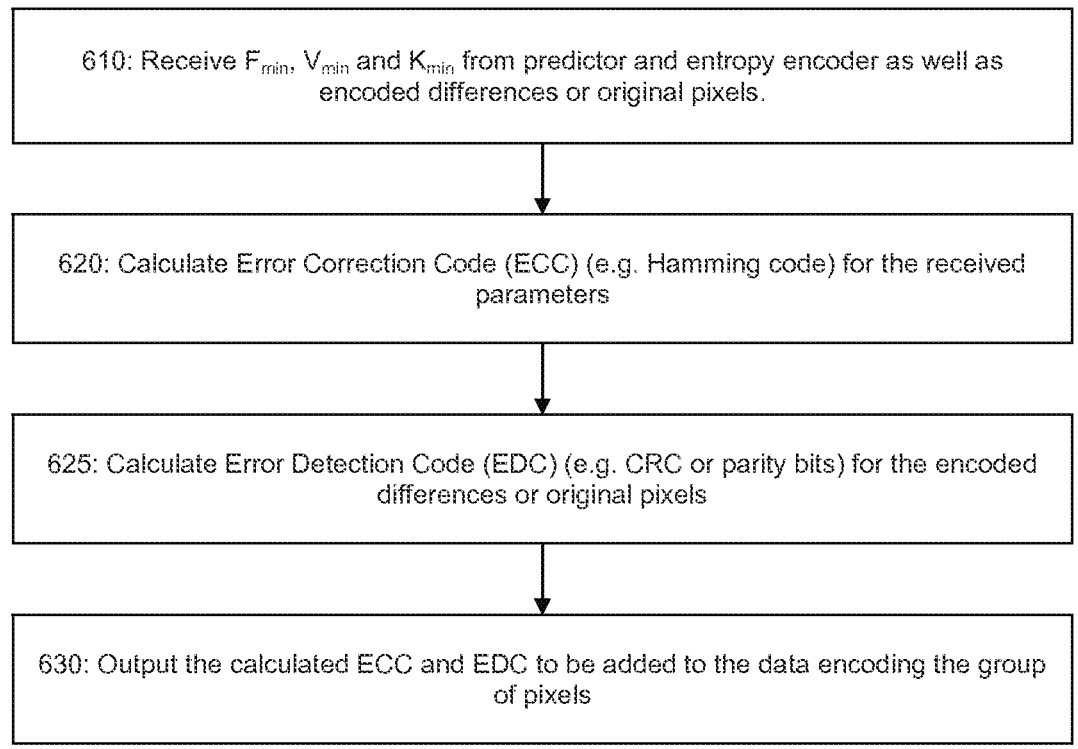
FIG. 6 illustrates a flowchart with relevant steps of a procedure for generating error protection data to be attached to the output of an entropy encoding algorithm.

Reference is now made to FIG. 6 which depicts an exemplary embodiment of an Error Protector flow chart.

The Error Protector may receive either a group of original pixels (as a group of size G, where G may be 16 for example) or a group of Golomb-Rice encoded differences together with $F_{min}$, the reference frame index (see description of the Predictor flow chart in FIG. 3), $V_{min}$, the offset vector within the reference frame (see description of the Predictor flow chart in FIG. 3) and $K_{min}$, the Golomb-Rice encoding parameter (see description of the Entropy Encoder flow chart in FIG. 5) 610. If the Entropy Encoder also uses a P bit as discussed above to indicate mere truncated least significant bit encodings, it too may be forwarded to the Error Protector.

The Error Protector may calculate an Error Correction Code (ECC) to protect the parameters passed to it with the incoming data 620. In one embodiment such error correction code may be a Hamming (15,11) code if $F_{min}$ is expressed by one bit, $V_{min}$ is expressed by six bits, $K_{min}$ is expressed by three bits and one P bit is used. Under such an encoding, to the 11 bits constituting $F_{min}$, $V_{min}$ and $K_{min}$ an additional 4 bits, the ECC, are added such that any single bit error on the parameters and added ECC can be corrected by a receiver of the data. In another embodiment, where no $F_{min}$, $V_{min}$ or P bits are used (i.e. every pixel is referenced to a single pixel within a fixed prior frame and no Golomb-Rice optimizations are used) a three bit $K_{min}$ may be protected against single bit errors by a Hamming (7,4) code. In yet another embodiment, ECC's used may be one of many known error correction codes in the art.

In another embodiment, in addition to the ECC, an Error Detection Code (EDC) may be added, such as a Cyclic Redundancy Check (CRC) or a parity bit covering the encoded differences or pixel data 625. Such EDC may serve to detect errors in the data such that a decompressor may request the compressor to retransmit corrupted data in the rare case of uncorrectable errors.

It is noted, that by applying an ECC only to the parameters accompanying the pixel data (or the encoded differences representing them) very little overhead is added to the data stream. In addition, since no or very little dependency may exist between pixels at different coordinates within different frames (for example if $V_{min}$ and $F_{min}$ aren't used or are always constant), any bit error in the data stream may be limited to a single pixel (or pixels at the same coordinates within a sequence of frames) while most or all cross-pixel effects are eliminated by the error correction code that is applied to the bits that are effectively shared by multiple pixel encodings within a group—the F, V, K and P parameters. As a result, for medical applications, such error correction measures may be sufficient in protecting the data of CT scans while eliminating the need for an error correction scheme that is applied to all compressed data, resulting in the deterioration of effective compression ratios.

In another embodiment the number of bits representing the encoded differences or pixels may be represented by B which may also be attached to the group of encoded differences or pixels. The ECC may also be applied to B in order to allow easier synchronization on group data in the event of an error. B may simply count the bits of the represented pixels or differences or may only count the variable length of such encoding such as the unary represented parts of Golomb-Rice encoded bits.

In a further embodiment, if there is unused bandwidth, the amount of ECC may be increased to increase the protection, pixels may be transmitted in their original form, less processing intensive compression vectors V may be used or any combination of the above.

Finally, the output of the Error Protector is the group of encoded differences or pixels together with the parameters F, V, K and P and the calculated ECC and optionally an EDC 630. In a further embodiment the output of the error protector may be scrambled to adapt it to a specific slip ring transfer characteristic.

It is noted that the overhead per encoded pixel is governed by the size of the F, V, K and P parameters but may be tuned to any required minimum by altering the size G of the pixel groups processed together. The larger G, the smaller the overhead of the parameters but the higher the probability that compression ratios are limited due to lack of correlation between the pixels within the group. Likewise, the smaller G, the higher the overhead of the parameters but the smaller the probability that compression ratios are limited due to lack of correlation between the pixels within the group.

Figure 7:
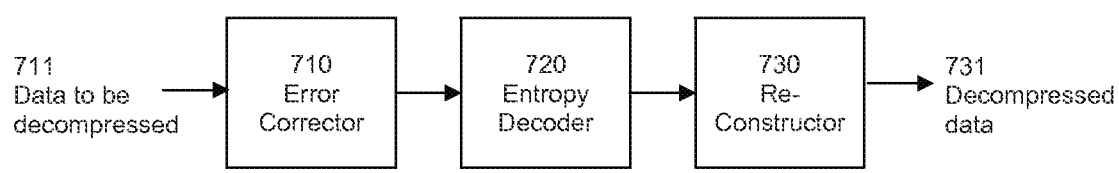
FIG. 7 is a block diagram with relevant elements of a decompressor system.

Reference is now made to FIG. 7 which depicts an exemplary embodiment of a decompressor (such as 130 in FIG. 1). Such a decompressor may be employed for image decompression as well as other types of data. In the context of this application data to be decompressed will be referred to as pixels representing single elements within an image. However, it should be appreciated that other types of data may also be decompressed in similar fashion even if such data doesn't represent an image. For instance, such data may represent any type of data including digitally sampled data from a variety of sources such as light, electromagnetic radiation or audio.

The decompressor in FIG. 7 comprises an Error Corrector 710 that receives the data 711 to be decompressed in the format of encoded differences or pixels together with encoding and error protected parameters as well as synchronization information regarding the beginning and end of the data received and the anticipated dimensions and form of frames to be received. The Error Corrector may be responsible for identifying and correcting any errors within the incoming data based on the Error Correction and Detection Codes used and stripping the ECC and EDC information from the data before passing it on to an Entropy Decoder 720. The Entropy Decoder may receive the encoded differences or original pixels together with the encoding parameters. It may be responsible for decoding the information into plain signed differences to be added or subtracted from reference data by a Re-constructor 730. If original pixel data is received by the Entropy Encoder (in the case that no compression has been applied to the pixels) it may forward such pixels as they are to the Re-constructor. The Re-constructor may reconstruct the original pixel data by adding or subtracting the differences from the appropriate reference data it may have stored in its memory. Then, it may store the reconstructed data for future reference in its memory and then forward it in the form of pixels as the output 731 of the decompressor.

Figure 8:
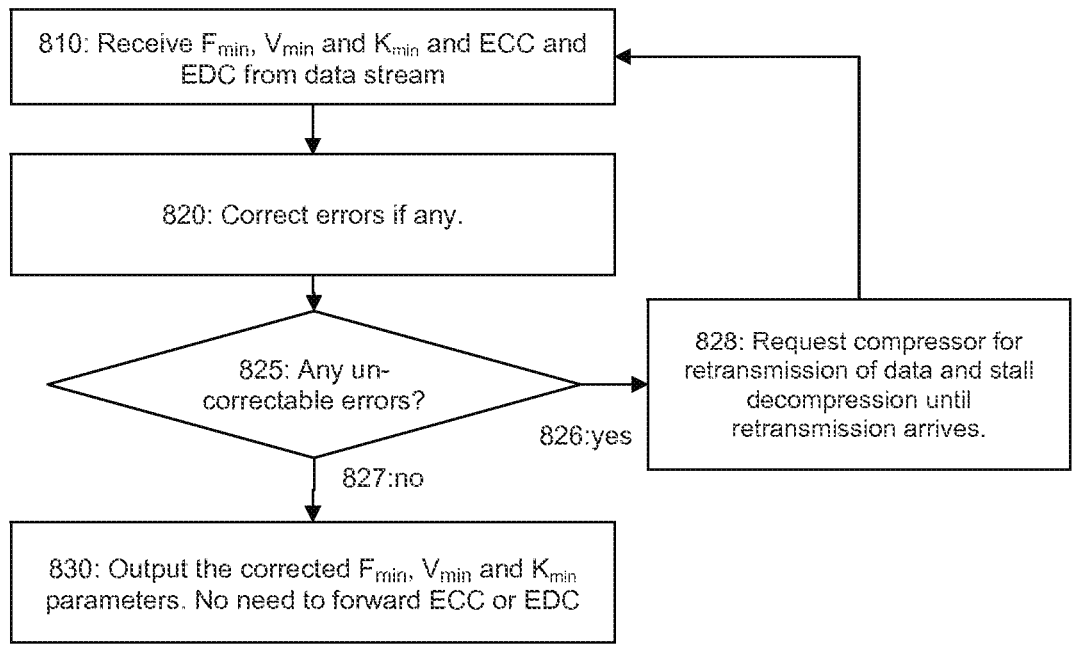
FIG. 8 illustrates a flowchart with relevant steps of a procedure for correcting errors on parameters sent with error correction data.

Reference is now made to FIG. 8 which depicts an exemplary embodiment of an Error Corrector flow chart.

The Error Corrector may receive all the encoding parameters sent together with groups of pixels as well as an Error Correction and Error Detection Code 810. These parameters may include the $F_{min}$, $V_{min}$, $K_{min}$ and P parameters as described above or a subset of such parameters as used by the compressor. Using the ECC code which may be any of the codes described above it may detect and correct one or more bit errors on the provided parameters 820. In an exemplary embodiment only a four bit $K_{min}$ is sent to the error corrector together with a three bit ECC computed by Hamming (7,4). The error correction procedure for such code is well known in the art. Using the EDC which may be of any of the codes described above it may detect errors on the provided groups of pixels or differences. In the event that a non-recoverable error is detected 825, 826, the Error Corrector may initiate a request for a retransmission of the corrupted data 828. For such request any common communications channel may be used from the decompressor to the compressor including low speed channels such as I^2C or Ethernet channels. In such event, decompression may be stalled until retransmitted data is received. Finally, assuming no uncorrectable errors are detected 827, the corrected parameters may be forwarded to the Entropy Decoder 830. At this point, the ECC may be discarded since it has no further use within the decompressor.

Figure 9:
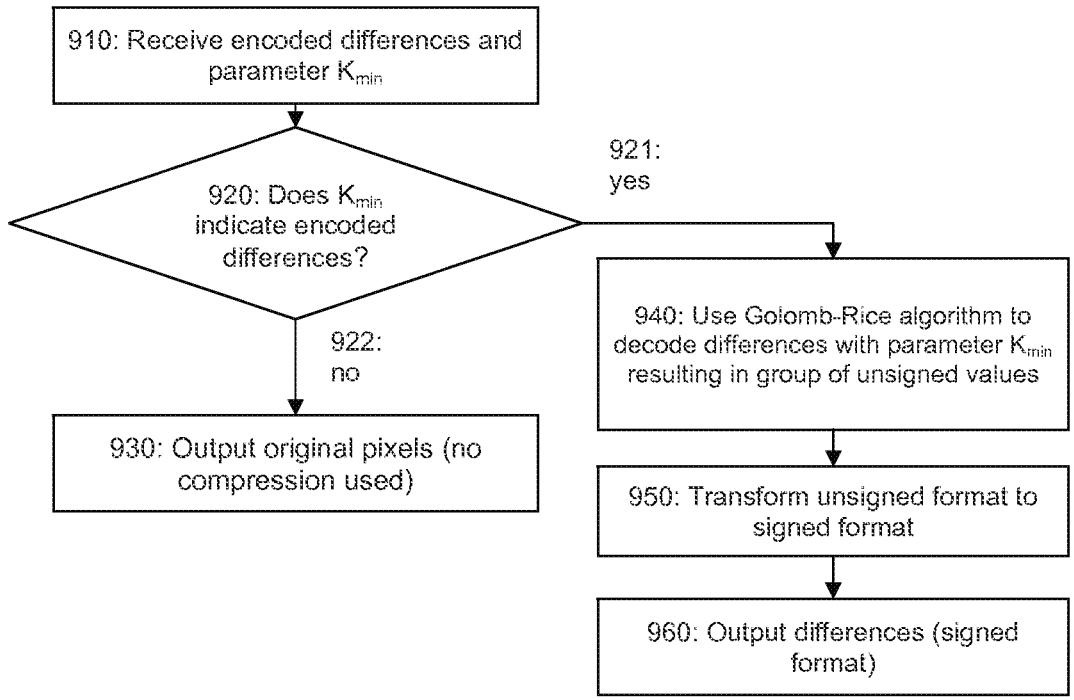
FIG. 9 illustrates a flowchart with relevant steps of a procedure for entropy decoding of a group of differences generated by a prediction algorithm and encoded by an entropy encoding algorithm with given parameters.

Reference is now made to FIG. 9 which depicts an exemplary embodiment of an Entropy Decoder flow chart.

The Entropy Decoder may receive groups of encoded differences from the Error Corrector together with the $K_{min}$ and possibly with a P parameter as described above 910. Alternatively, the parameters presented to the Entropy Decoder may indicate that the data is an uncompressed group of pixels (this may be encoded as a special value of $K_{min}$ as described above). If the input represents uncompressed data 920, 922 it is output as is and the $K_{min}$ and P parameters may be discarded 930. If the input represents differences 921, the data is decoded by a set of steps which represent the reverse action of the Entropy Encoder as presented above. This is described below.

Using the $K_{min}$ parameter (which may be encoded), the Entropy Decoder may decode the differences encoded by the Golomb-Rice code 940. For example, given a bit stream and a parameter $K_{min}$, the first $K_{min}$ bits are used as least significant bits of a new difference value, then the number of ones is counted until the first zero bit to deduce the value of the most significant bits which may be added to the previously mentioned least significant bits. This process is repeated G times for a pixel group of size G as predefined or as negotiated between the compressor and decompressor. For instance, given a binary code $01110101110_b$ and $K_{min}=2$, the first difference may be identified as having least significant bits of $01_b$ and most significant bits of $10_b$ (this stands for 2 which is the number of ones following the least significant bits) and together the value $1001_b$ emerges which is 9 in decimal notation. The next difference is decoded as having $10_b$ as least significant bits and most significant bits of $11_b$ (this stands for 3 which is the number of ones following the least significant bits) which results in $1110_b$ or 14 in decimal notation.

Next, the Entropy Decoder may transform the resulting differences which are all expressed as positive integers back into signed format 950. This may be done using the reverse formula of the one used by the Entropy Encoder to transform signed values into positive integers. For example, even integers N=2*D (where D is a non-negative integer) are transformed via D=N/2 into non-negative differences D while odd integers N=−2*D−1 (where D is a negative integer less than zero) are transformed via D=−(N+1)/2 into negative differences D. Thus, differences such as 9 and 14 as decoded above are transformed into −5 and 7. It is appreciated that other transformations are also possible, depending on the technique used by the corresponding Entropy Encoder.

If a P parameter is used as defined above indicating no non-zero most significant bits, the bit stream for a group of differences of size G may be simply decoded by partitioning the incoming $G*K_{min}$ bits into G equal bit groups representing the positive representation of the differences and from there transformation continues as above.

Finally, the Entropy Decoder may output the signed differences towards the Re-constructor 960 as described in FIG. 7. As mentioned above, if the input into the Entropy Decoder is composed of non-compressed pixels, these are forwarded as is to the Re-Constructor.

Figure 10:
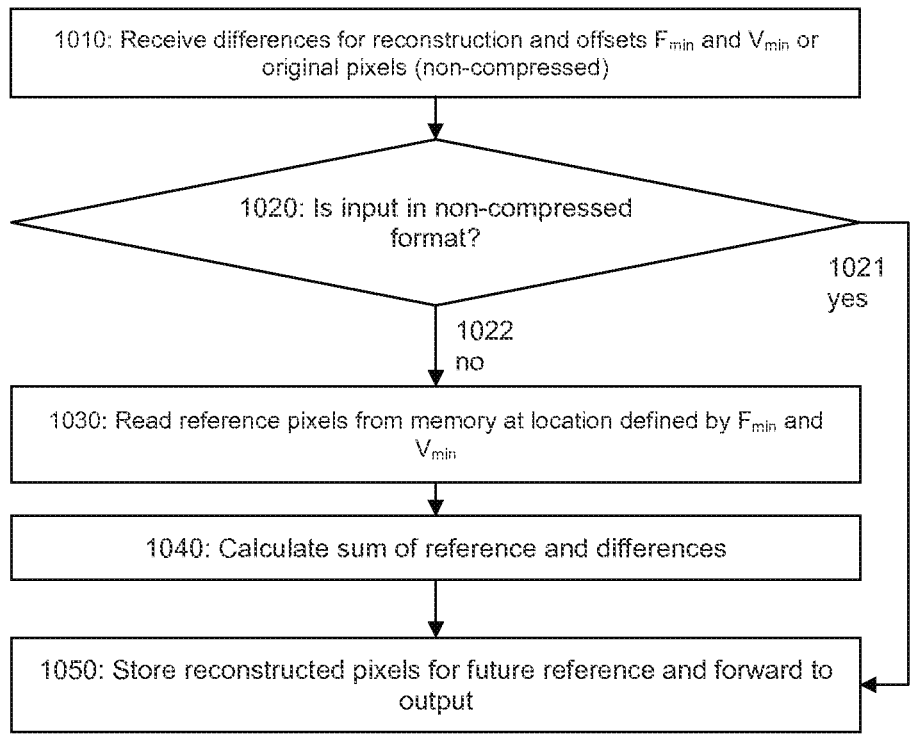
FIG. 10 illustrates a flowchart with relevant steps of a procedure for reconstructing pixel groups from a group of decoded differences referencing a given offset within data stored in memory.

Reference is now made to FIG. 10 which depicts an exemplary embodiment of a Re-Constructor flow chart.

The Re-Constructor may receive inputs for a group of pixels either in non-compressed format or in the form of differences as received from the Entropy Decoder 1010.

In the case where a pixel group arrives as non-compressed pixels to the Re-Constructor 1020, 1021 it may merely store them for future reference at a location that may be calculated by the Re-Constructor or explicitly carried with the incoming data and output them as the decompressed output of the Decompressor 1050. If the number of reference frames used by the Predictor (see 210 of FIG. 2) is F, the Re-Constructor may also store a history of F frames which may be overwritten in a First-In First-Out (FIFO) order such that the oldest frame held in memory is always overwritten by new incoming decompressed pixels. Thus, the memory used by the decompressor may be limited to F frames. A typical number F would be 3 such that new pixels are written over pixels three frames in the past.

Figure 4:
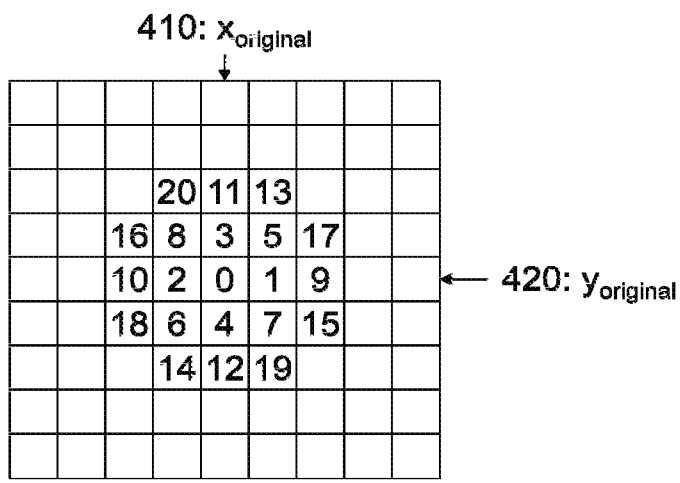
FIG. 4 illustrates a method for efficiently defining offsets in a 2-dimensional array of pixels.

In the event the Re-Constructor receives differences of pixels and parameters $F_{min}$ and $V_{min}$ as defined above and not in non-compressed format 1020, 1022 it may proceed by first reading the required reference pixels from its memory at the location defined by $F_{min}$ and $V_{min}$ 1030. $F_{min}$ and $V_{min}$ as defined above may indicate the location of reference data within a memory holding previously transmitted pixels, where $F_{min}$ may indicate the frame to be used as reference and $V_{min}$ an encoded vector within the reference frame relative to the current location of pixels being decompressed pointing to the exact pixels to be used as reference. $V_{min}$ may use an encoding table as depicted in FIG. 4 and its value may in turn be encoded by a Golomb-Rice code with a known K parameter. In the latter case, the value of $V_{min}$ may first be decoded into a positive integer which may be decoded into (x,y) offsets within the reference frame.

Next, the Re-Constructor may reconstruct the compressed pixels by adding the differences to the correct reference pixel read from memory 1040. This operation may be performed per pixel or for all pixels in a group at once.

Again, once the pixels have been reconstructed, they may be stored in memory for future reference and sent as output of the Re-Constructor 1050 and output of the Decompressor (see 730 in FIG. 7).

It is appreciated that all the above methods for compression and decompression of pixel data are independent of image dimensions. In particular, it should be noted that at the loss of certain vector V values as described above, the above method may be performed in parallel on different parts of a pixel stream independently. Thus, a parallel implementation such as an FPGA or ASIC implementation may be used to accelerate both compression and decompression.

It will be appreciated that the above described methods may be varied in many ways, including, changing the order of steps, and the exact implementation used. It should also be appreciated that the above described description of methods and apparatus are to be interpreted as including apparatus for carrying out the methods and methods of using the apparatus.

Figure 11:
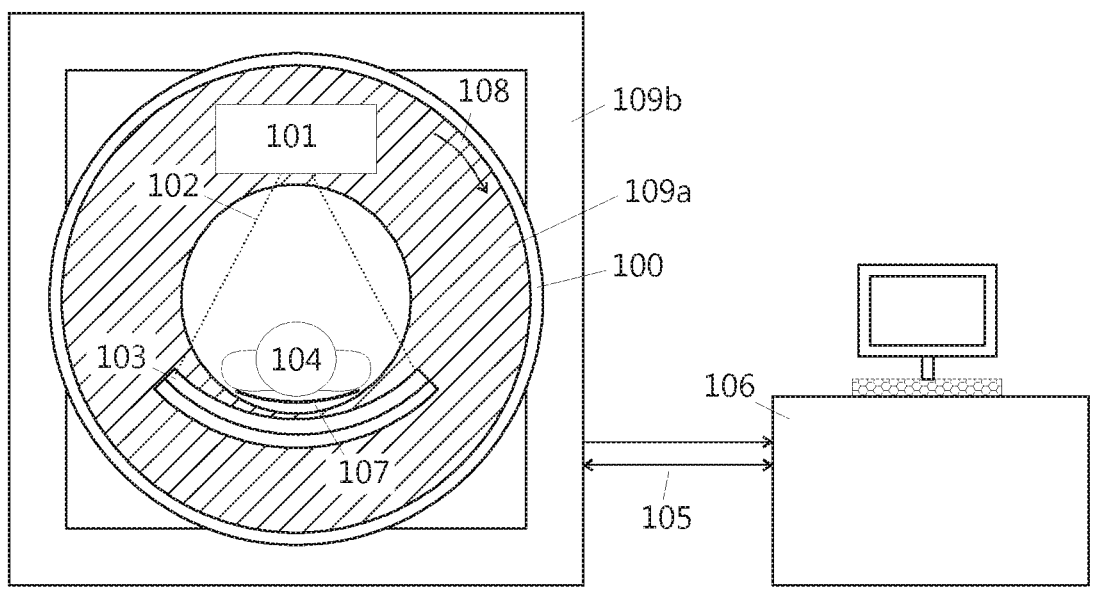
FIG. 11 shows a computer tomograph.

FIG. 11 shows a computer tomograph. The computer tomograph (CT scanner) includes two mechanical main parts. A stationary platform 109b serves as a base and support for the entire instrument in which a rotating platform 109a rotates. A patient 104 is positioned on a bed 107 in an opening of the rotating part. An X-ray tube 101 and also a detector 103 disposed oppositely thereto are provided for scanning the patient by means of X-rays 102. The X-ray tube 101 and the detector 103 are disposed to be rotatable on the rotating platform 109a. A slip ring 100 serves as an electrical connection between the rotating platform 109a and the stationary platform 109b. The compressor (not shown here) is preferably located at the rotating platform 109a, while the decompressor (also not shown here) may be located at the stationary platform 109b. An evaluation and control unit 106 serves for operating the computer tomograph and also for displaying the generated images. The decompressor (not shown here) may also be located at the evaluation and control unit 106. For communication with the computer tomograph a data link 105 like a computer network is provided.

It will be appreciated to those skilled in the art having the benefit of this disclosure that this invention is believed to provide data compressors and decompressors as well as compression methods and decompression methods. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A data-transferring slip ring system comprising:
a data compressor positioned on a rotating platform, the data compressor having input and output and configured to be operably connectable to and to receive data at the input from a data generator, said data compressor including
a predictor unit,
an entropy encoder unit, and
an error protector unit,
wherein said predictor unit, entropy encoder unit, and error protector unit are adapted to be in data-transfer communication with one another;
a data decompressor positioned on a stationary platform and configured to be operably connectable to a target; and
a slip ring operably connecting and configured to transfer data between the output of said data compressor and said data decompressor,
wherein said predictor unit includes means for processing data, received at the input, in groups of data pixels and means for predicting data to be compressed based on
(i) F previously stored data frames and
(ii) one or more coordinates of data pixels within said data frames expressed as a coordinate vector V encoded as a positive integer;
wherein said entropy encoder unit is adapted to encode the data to be compressed as predicted by the predictor unit;
wherein said error protector unit is adapted (i) to embed error-correction code into the encoded data to protect one or more of an encoding parameter $K_{min}$, of the Golomb-Rice encoding for which a minimal encoding size is achieved, an index $F_{min}$ of a reference data frame, and a coordinate offset vector $V_{min}$ corresponding to said reference frame and (ii) to transfer the data with embedded error-correction code to the output,
wherein said predictor unit is adapted to select the best prediction per group of data pixels determined by the index $F_{min}$ of a reference data frame and the offset vector $V_{min}$ within the reference data frame; and
wherein said entropy encoder is adapted to encode the best prediction's location in history and a difference between the prediction and the incoming data using a set of parameters $K_{min}$ and P added into the output data stream.

2. A slip ring system according to claim 1, wherein the means for prediction of data to be compressed includes means for prediction based on a data frame that precedes the last of said F previously stored data frames.

3. A slip-ring system according to claim 1, wherein the means for processing data includes means for one-step processing of groups of pixels associated with a single image row or a single image column.

4. A slip ring system according to claim 1, wherein the entropy encoder unit is adapted
   to encode groups of differences between history and incoming data using Golomb-Rice encoding with a parameter $K_{min}$ and,
   in the event that said Golomb-Rice encoding results in compressed data the amount of which exceeds the amount of non-compressed data, to transfer non-compressed data to the error protection unit.

5. A slip-ring system according to claim 4, wherein said parameter $K_{min}$ is different for each group of differences.

6. A slip ring system according to claim 4, wherein the encoding parameter $K_{min}$ is encoded with the data it applies to using minimal encoding indicating that no data compression is used.

7. A slip ring system according to claim 1, wherein the entropy encoder unit is adapted to transfer data in non-compressed format once every S frames.

8. A slip ring system according to claim 7, wherein the entropy encoder unit is adapted to select a subset of data pixel groups for transferring data in non-compressed format by choosing a data pixel group every S groups, where S is a prime number that is not a prime factor of the number of groups in a single data frame.

9. A slip ring system according to claim 1, wherein the predictor unit is adapted to transfer data in a compressed format once every S frames by predicting the incoming data pixels based on a fixed value instead of previously stored frames.

10. A slip ring system according to claim 9, wherein the entropy encoder unit is configured to transfer data in non-compressed format for a subset of data pixel groups within every frame.

11. A slip ring system according to claim 9, wherein said error protector unit is adapted to protect a subset of data being sent with the encoded data by error correction code.

12. A slip ring system according to claim 9, wherein at least one of $K_{min}$, $F_{min}$ and $V_{min}$ is protected with said error correction code.

13. A computed tomography (CT) scanner comprising a slip ring system according to claim 1, wherein the data compressor is operably connected to a data generator that includes a digital sampler of analog signals received by a signal receiver from an X-ray detector.

14. A method for compressing sampled analog data comprising:
   receiving and processing, with a data processing system, data in the form of pixels, said data pixels associated with an image frame and locations within the image frame;
   predicting data based on a reference to one or more of F previously stored image frames and one or more of multiple coordinates within said F previously stored image frames expressed with a vector V that is encoded as a positive integer to form predicted data;
   encoding the predicted data with an entropy encoder to form encoded data;
   error-protecting at least a part of said encoded data and transferring a subset of said encoded data with error correction code including one or more of:
      (i) an encoding parameter $K_{min}$, of the Golomb-Rice encoding, for which a minimal encoding size is achieved,
      (ii) an index $F_{min}$ of a reference data frame, and
      (iii) a coordinate offset vector $V_{min}$ corresponding to said reference data frame;
   selecting the best prediction per pixel group and encoding its location in history determined by the reference frame index $F_{min}$ and the offset vector $V_{min}$ within the reference data frame; and
   encoding a difference between the best prediction and incoming data using a set of parameters $K_{min}$ and P added into an output data stream.

15. A method according to claim 14, wherein said predicting includes predicting with a means for prediction based on a data frame that precedes the last of F previously stored data frames.

16. A method according to claim 14, wherein said processing includes processing with a means for one-step processing of groups of pixels associated with a single image row or a single image column.

17. A method according to claim 14, wherein said vector V is encoded using Golomb-Rice encoding with a parameter $K_v$.

18. A method according to claim 14, further comprising one or more of
   (i) encoding groups of differences received using Golomb-Rice encoding with a parameter $K_{min}$ which may be different for every group of differences and
   (ii) forwarding data as is in non-compressed format in the event that Golomb-Rice encoding results in more data than non-compressed data.

19. A method according to claim 18, wherein the parameter $K_{min}$ is encoded, with data it applies to, using a minimal encoding that also indicates a case where no compression is used.

20. A method according to claim 14, further comprising transferring data in non-compressed format once every S frames.

21. A method according to claim 20, wherein said transferring data includes selecting a subset of pixel groups by choosing a pixel group every S groups, wherein S is a prime number that is not a prime factor of the number of groups in a single data frame.

22. A method according to claim 14, wherein further comprising transferring data in a compressed format once every S frames by predicting the incoming data pixels based on a fixed value instead of previously stored frames.

23. A method according to claim 22, further comprising transferring data in non-compressed format for a subset of pixel groups within every frame.

24. A method according to claim 14, further comprising limiting a subset of data being error protected to at least one of said $K_{min}$, $F_{min}$ and $V_{min}$.

25. A data-transferring slip ring system comprising:
   a data compressor positioned on a rotating platform, the data compressor having input and output and configured to be operably connectable to and to receive data at the input from a data generator, said data compressor including
      a predictor unit,
      an entropy encoder unit, and
      an error protector unit,
      wherein said predictor unit, entropy encoder unit, and error protector unit are adapted to be in data-transfer communication with one another;
   a data decompressor positioned on a stationary platform and configured to be operably connectable to a target; and
   a slip ring operably connecting and configured to transfer data between the output of said data compressor and said data decompressor, wherein said predictor unit includes
means for processing data, received at the input, in groups of data pixels and
means for predicting data to be compressed based on
(i) F previously stored data frames and
(ii) one or more coordinates of data pixels within said data frames expressed as a coordinate vector V encoded as a positive integer;
wherein said entropy encoder unit is adapted to encode the data to be compressed as predicted by the predictor unit;
wherein said error protector unit is adapted
(i) to embed error-correction code into the encoded data to protect one or more of an encoding parameter $K_{min}$, of the Golomb-Rice encoding for which a minimal encoding size is achieved, an index $F_{min}$ of a reference data frame, and a coordinate offset vector $V_{min}$ corresponding to said reference frame, and
(ii) to transfer the data with embedded error correction code to the output,
and
wherein the entropy encoder unit is adapted
to encode groups of differences between history and incoming data using Golomb-Rice encoding with a parameter $K_{min}$ and,
in the event that said Golomb-Rice encoding results in compressed data the amount of which exceeds the amount of non-compressed data, to transfer non-compressed data to the error protection unit.

26. A slip-ring system according to claim 25, wherein said parameter $K_{min}$ is different for each group of differences.

27. A slip ring system according to claim 25, wherein the encoding parameter $K_{min}$ is encoded, with data it applies to, using minimal encoding indicating that no data compression is used.

28. A slip ring system according to claim 25, wherein the entropy encoder unit is adapted to transfer data in non-compressed format once every S frames.

29. A slip ring system according to claim 25, wherein the entropy encoder unit is adapted to select a subset of data pixel groups for transferring data in non-compressed format by choosing a data pixel group every S groups, where S is a prime number that is not a prime factor of the number of groups in a single data frame.

30. A slip ring system according to claim 25, wherein the predictor unit is adapted to transfer data in a compressed format once every S frames by predicting the incoming data pixels based on a fixed value instead of previously stored frames.

31. A slip ring system according to claim 25, wherein the entropy encoder unit is configured to transfer data in non-compressed format for a subset of data pixel groups within every frame.

32. A slip ring system according to claim 25, wherein at least one of $K_{min}$, $F_{min}$ and $V_{min}$ is protected with said error correction code.

33. A computed tomography (CT) scanner comprising a slip ring system according to claim 25, wherein the data compressor is operably connected to a data generator that includes a digital sampler of analog signals received by a signal receiver from an X-ray detector.

34. A method for compressing sampled analog data comprising:
receiving and processing, with a data processing system, data in the form of pixels, said data pixels associated with an image frame and locations within the image frame;
predicting data based on a reference to one or more of F previously stored image frames and one or more of multiple coordinates within such image frames expressed with a vector V that is encoded as a positive integer, to form predicted data;
encoding the predicted data with by an entropy encoder to form encoded data;
error-protecting at least a part of said encoded data and transferring a subset of said encoded data with error correction code including one or more of:
an encoding parameter $K_{min}$, of the Golomb-Rice encoding, for which a minimal encoding size is achieved,
an index $F_{min}$ of a reference data frame, and
a coordinate offset vector $V_{min}$ corresponding to said reference data frame;
performing at least one of:
(i) encoding groups of differences received using Golomb-Rice encoding with a parameter $K_{min}$ which may be different for each group of differences, and
(ii) forwarding data as is in non-compressed format in the event that Golomb-Rice encoding results in more compressed data than non-compressed data.

35. A method according to claim 34, wherein the parameter $K_{min}$ is encoded, with data it applies to, using minimal encoding that also indicates the case where no compression is used.

36. A method according to claim 34, wherein said prediction includes predicting with a means for prediction based on a data frame that precedes the last of F previously stored data frames.

37. A method according to claim 34, wherein said processing includes processing with a means for one-step processing of groups of pixels associated with a single image row or a single image column.

38. A data-transferring slip ring system comprising:
a data compressor positioned on a rotating platform, the data compressor having input and output and configured to be operably connectable to and to receive data at the input from a data generator, said data compressor including
a predictor unit,
an entropy encoder unit, and
an error protector unit,
wherein said predictor unit, entropy encoder unit, and error protector unit are adapted to be in data-transfer communication with one another;
a data decompressor positioned on a stationary platform and configured to be operably connectable to a target; and
a slip ring operably connecting and configured to transfer data between the output of said data compressor and said data decompressor,
wherein said predictor unit includes
means for processing data, received at the input, in groups of data pixels and
means for predicting data to be compressed based on
(i) F previously stored data frames and
(ii) one or more coordinates of data pixels within said data frames expressed as a coordinate vector V encoded as a positive integer;
wherein said entropy encoder unit is adapted to encode the data to be compressed as predicted by the predictor unit;
wherein said error protector unit is adapted
(i) to embed error-correction code into the encoded data to protect one or more of an encoding parameter $K_{min}$, of the Golomb-Rice encoding for which a minimal encoding size is achieved, an index $F_{min}$ of a reference data frame, and a coordinate offset vector $V_{min}$ corresponding to said reference frame, and
(ii) to transfer the data with embedded error correction code to the output, and the entropy encoder unit is adapted to transfer data in non-compressed format once every S frames, and to select a subset of data pixel groups for transferring data in non-compressed format by choosing a data pixel group every S groups, where S is a prime number that is not a prime factor of the number of groups in a single data frame.

39. A method for compressing sampled analog data comprising:

receiving and processing, with a data processing system, data in the form of pixels, said data pixels associated with an image frame and locations within the image frame;

predicting data based on a reference to one or more of F previously stored image frames and one or more of multiple coordinates within such image frames expressed with a vector V that is encoded as a positive integer, to form predicted data;

encoding the predicted data with an entropy encoder to form encoded data;

error-protecting at least a part of said encoded data and transferring a subset of said encoded data with error correction code including one or more of:
an encoding parameter $K_{min}$, of the Golomb-Rice encoding, for which a minimal encoding size is achieved,
an index $F_{min}$ of a reference data frame, and
a coordinate offset vector $V_{min}$ corresponding to said reference data frame;

transferring data in non-compressed format once every S frames, and wherein said transferring data includes selecting a subset of pixel groups by choosing a pixel group every S groups, wherein S is a prime number that is not a prime factor of the number of groups in a single data frame.

* * * * *